United States Patent
Haugland et al.

(10) Patent No.: US 6,366,815 B1
(45) Date of Patent: Apr. 2, 2002

(54) IMPLANTABLE NERVE STIMULATOR ELECTRODE

(75) Inventors: Morten Haugland; Hans Harding, both of Aalborg (DK)

(73) Assignee: Neurodan A/S, Aalborg (DK)

( * ) Notice: Subject to any disclaimer, the term of this patent is extended or adjusted under 35 U.S.C. 154(b) by 0 days.

(21) Appl. No.: 09/331,838

(22) PCT Filed: Jan. 13, 1998

(86) PCT No.: PCT/DK98/00010

§ 371 Date: Aug. 18, 1999

§ 102(e) Date: Aug. 18, 1999

(87) PCT Pub. No.: WO98/30279

PCT Pub. Date: Jul. 16, 1998

(30) Foreign Application Priority Data

Jan. 13, 1997 (DK) .................................................. 0044/97

(51) Int. Cl.[7] .................................................. A61N 1/36
(52) U.S. Cl. .................................................. 607/48; 607/118
(58) Field of Search .................................................. 607/118, 40, 30, 607/32, 41, 45, 46, 61, 48, 49, 36, 116; 128/903

(56) References Cited

U.S. PATENT DOCUMENTS

| | | | |
|---|---|---|---|
| 3,522,811 A | * 8/1970 | Schwartz et al. | 607/27 |
| 3,867,950 A | * 2/1975 | Fischell | 607/118 |
| 4,608,985 A | 9/1986 | Crish et al. | |
| 4,932,405 A | 6/1990 | Peeters et al. | |
| 4,940,065 A | * 7/1990 | Tanagho et al. | 607/118 |
| 5,199,428 A | 4/1993 | Obel et al. | |
| 5,309,096 A | * 5/1994 | Hoegnelid | 324/256 |
| 5,358,514 A | * 10/1994 | Schulman et al. | 607/61 |

FOREIGN PATENT DOCUMENTS

| | | |
|---|---|---|
| GB | 2 239 802 | 7/1991 |
| WO | 92/15366 | 9/1992 |

* cited by examiner

Primary Examiner—Kennedy Schaetzle
(74) Attorney, Agent, or Firm—Dykema Gossett PLLC

(57) ABSTRACT

The invention relates to an implantable stimulator electrode for stimulation of nerves adapted to be surgically implanted around a nerve bundle, said stimulator comprising one or more electrode means which, when implanted around said nerve bundle, surrounds the nerve bundle totally or partly. Electrode means and electronic circuit means are coupled to and powered by one or more receiving coils mounted on the stimulator housing. One advantage of the invention is that the electrode, when implanted, acts as a remote addressable maintenance free unit.

9 Claims, 4 Drawing Sheets

IMPLANTABLE NERVE STIMULATOR ELECTRODE

BACKGROUND OF THE INVENTION

The invention relates to an implantable electrode for stimulation of nerves adapted to be surgically implanted around a nerve bundle.

Restoring motor-functions of (partially) paralysed people is known by exploiting the fact that muscles respond to electrical energy. This principle can be utilised to directly stimulate muscles or to stimulate the nerves leading to the muscles. Direct stimulation of muscles requires a number of electrodes distributed on the muscle, compare e.g. U.S. Pat. No. 5,314,458, and is relatively power consuming. In addition, the control equipment is rather complicated for surveillance of the electrodes to achieve the desired movement of the muscle.

Stimulation of nerves can be made by placing electrodes locally around the nerves which is known from e.g. U.S. Pat. No. 5,038,781. For this reason the surgical intervention is minor. Stimulation of nerves also requires much less energy than stimulation of muscles although the power requirement is still high compared to e.g. a pacemaker due to the higher stimulation frequency necessary to obtain smooth contractions of muscles. The present invention relates to nerve stimulation.

The controlling equipment and the power supply are placed externally on the human body and could be connected to the electrodes by using wires passing through the skin which for obvious reasons is not an attractive solution. Alternatively, the placement of a transmitter on the body and an implant of a receiver in the body wired to the electrodes is also known, said transmitter sending signals and energy through the skin and flesh to the receiver. More specifically, the present invention relates to the latter type of stimulator electrodes.

Such a neurological stimulation apparatus is known from e.g. U.S. Pat. No. 5,038,781 said apparatus comprising nerve cuffs with electrodes attached to a nerve bundle and wire connected to an implant case containing the electronic circuitry receiving operating power and information signals by radio frequency coupling to an external unit. Running wires under the skin and implanting a casing in the body is for obvious reasons not an attractive solution.

Another example is known from U.S. Pat. No. 4,057,069 which deals with an implantable nerve stimulator receiving energy from an external unit by telemetrically transferring energy from an external unit. The nerve stimulator contains a detector circuit which by an adequate excitation can address a number of electrode pairs of a multiplexer. The nerve stimulator has among other things the disadvantage in connection with multielectrode systems of not being able to address all of these simultaneously, however, only sequentially. In addition, the nerve stimulator is limited locally, as the electrode pairs in question necessarily have to be in galvanic contact with the nerve stimulator itself.

A further example is known from U.S. Pat. No. 3,667,477 which deals with an implantable nerve stimulator which receives energy from an external unit by telemetric transmission. The implantation of the disclosed nerve stimulator, however, is quite complicated, as the stimulator is made of separate receiving and electrode means coupled by leads.

It could be mentioned that it is also known to stimulate muscles by means of telemetric transmission.

An example is known from U.S. Pat. No. 5,314,458 which deals with an implantable muscle stimulator which receives energy from an external unit by telemetric transmission. This unit can be addressed individually, however, due to its placement on the muscle itself a very powerful excitation is needed and subsequently a very powerful electromagnetic field which causes the electromagnetic transfer of energy to be less attractive considering the continuing influence of the surrounding tissue. In addition, it is needed that the stimulator is being widely controlled when stimulating a muscle complex, as a certain number of specific controlled stimulators is needed in order to obtain an appropriate movement of the muscle.

SUMMARY OF THE INVENTION

One object of the present invention is to provide an improved and simplified neurological stimulation apparatus. A further object is to minimise the surgical intervention when applying the apparatus in the body.

When according to the present invention the input terminals coupled to one or more receiving coils are mounted on the stimulator housing, a remote individual addressable stimulator for stimulation of nerve bundles is obtained thus being able to function as an isolated implanted unit. When implanted, the stimulator will be placed in a juxta position or around the nerve being stimulated. According to the invention there is no need for any lead connections between the stimulator and external circuits, in the sense that the transmitter can be activated on location by remote signals without any need for an internal power source.

The control of the stimulator or the stimulators and the resulting activation of muscles is made even more simple due to the fact that a stimulation of the nerve often is less complicated than a stimulation directly on the muscles which are to be activated. In the case when a group of muscles or a muscle with multiple motor points innervated by the same nerve are wished to be activated at the same time (as for example in the case of dropfoot stimulation), it is advantageous to use one multichannel nerve stimulator placed on the nerve compared to many individual stimulators placed in the muscles.

According to the invention it is thus possible to obtain a remote stimulation using a minimal electromagnetic field.

Coupling the input terminals to one or more receiving coils mounted on the stimulator/electrode housing, it is possible to obtain a necessary power supply to the electrodes and the electronic circuit means which is provided telemetrically via the receiving coil or receiving coils, thus avoiding the use of lead connections between the internal part of the stimulator and the external part of the stimulator. It is thus possible to avoid battery powered electrodes.

Furthermore, the transmitter is basically free of maintenance in the sense that replacement of implanted power sources or the like is not needed.

In this connection, it is noted that the necessary effect needed to stimulate the nerves is approximately ten times lower than the necessary effect needed for direct stimulation of muscles. By stimulating the nerves rather than the muscles, a remote activation of the stimulator is particularly attractive.

The risk of complications due to the surgery activity required to implant the stimulator is moreover reduced in the sense that the stimulator itself, according to the invention, can be realised in a very compact design in contrary to e.g. lead-connected systems.

The stimulator according to the invention is especially applicable in situations where a continuing or periodically stimulation of the muscle is needed, as the implanted stimulator under constant influence of movement is mechanically as well as electronically stable and sturdy in the sense that neither the electrical nor the mechanical parts undergo stress during said movement which also results in a minimised risk of IN VIVO complications.

In addition, the use of an external power source will in practise result in a minimised risk of noise signals activating the stimulator as these external noise signals necessarily have to reach a certain noise level at a given wavelength in order to activate the electrodes of the stimulator.

Accordingly, in a further embodiment of the invention, the electrode means, when implanted around said nerve bundle, comprises one or more circle-shaped or semi-circumferential electrodes defining a contact area, each contact area being electrically coupled to the output terminals of the electronic circuit means. (Totally or partly surrounding the output terminals). This particular "shape" of the electrode means thus makes it possible to obtain a very well-defined positioning of the stimulator as regards the nerve bundle and at the same time, the electrode means create good contact between the electrode means and the nerve bundle.

When the electrode means, when implanted around said nerve bundle, comprises one or more ring-shaped electrodes totally or partly surrounding the nerve bundle, each ring-shaped electrode comprising at least two distinct electrode contact areas, each electrode area being electrically coupled to the output terminals of the electronic circuit means, it is possible to obtain a stimulator which is able to make a selective stimulation of the nerve and the associated muscles. The stimulation of the nerves can be obtained in various ways depending on which result is wanted. The stimulation can thus be obtained by a mono- or multipolar electrical stimulation, the chosen multipolar electrode stimulation being transverse, e.g. effected by electrodes on the same ring electrode or longitudinal, e.g. effected by electrodes on different rings. Furthermore, it is possible to combine transverse and longitudinal stimulation. The stimulator thus has the possibility of being used with an overall degree of selectivity which can be chosen from known mono- or multipolar configurations.

In a multichannel stimulator, each channel has its own electronic circuit connected to a separate receiver coil. The only difference between each channel is the resonance frequency of which each channel is active. The main purpose of the electronic circuit is to create an adequate stimulation pulse shape.

When each transmitter comprises one or more transmitting coils positioned in spaced relationships on each side of one or more of the stimulators, it is possible to obtain a very useful remote activated stimulator system.

BRIEF DESCRIPTION OF THE DRAWINGS

Below, the invention will be further explained with reference to the accompanying drawing, wherein.

DESCRIPTION OF A PREFERRED EMBODIMENT

Figure 1:
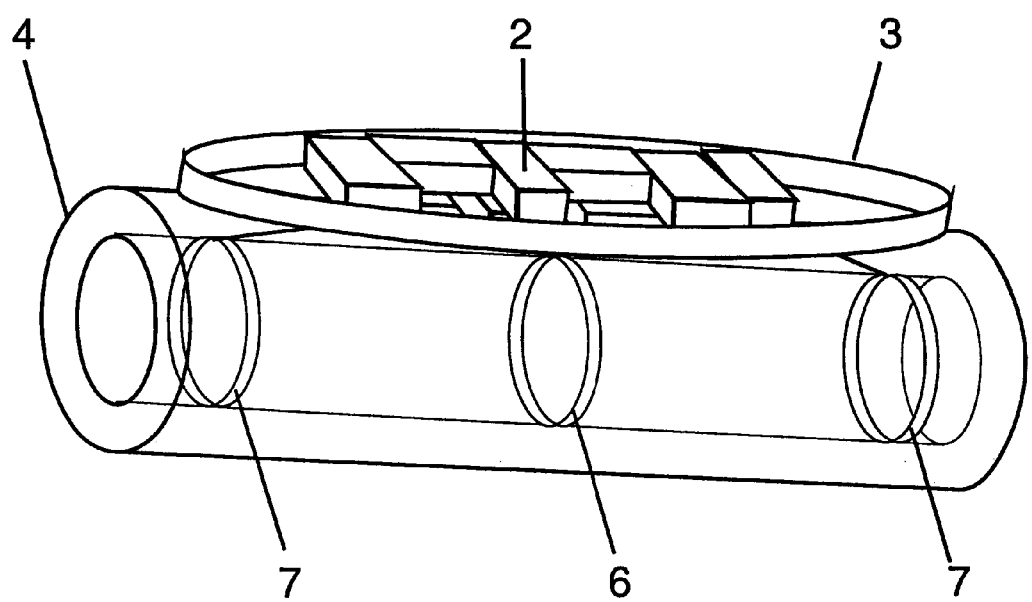
FIG. 1 shows a stimulator according to the invention.

Referring to FIG. 1 there is shown a stimulator according to the invention, said stimulator comprising a receiver coil 3 which is coupled to an electrical circuit 2. The electrical circuit 3 is furthermore connected to electrodes 6 and 7.

The electrode 6 is a feeding electrode coupled to one output terminal of the electrical circuit 3, while the electrodes 7 are return electrodes, coupled to the common output terminal of the electrical circuit.

The stimulator is encapsulated in a cuff made of a biologically inert substance 4 such as silicone rubber or the like. For placement of the cuff around a nerve, the cuff is slit length-wise in a zip-like manner.

The invention provides a very compact design of the stimulator by incorporating the receiving coil in the stimulator housing or stimulator body, and it is thus possible to implant the stimulator properly without the use of lead connection between co-operating stimulators or an external power supply.

Figure 2:
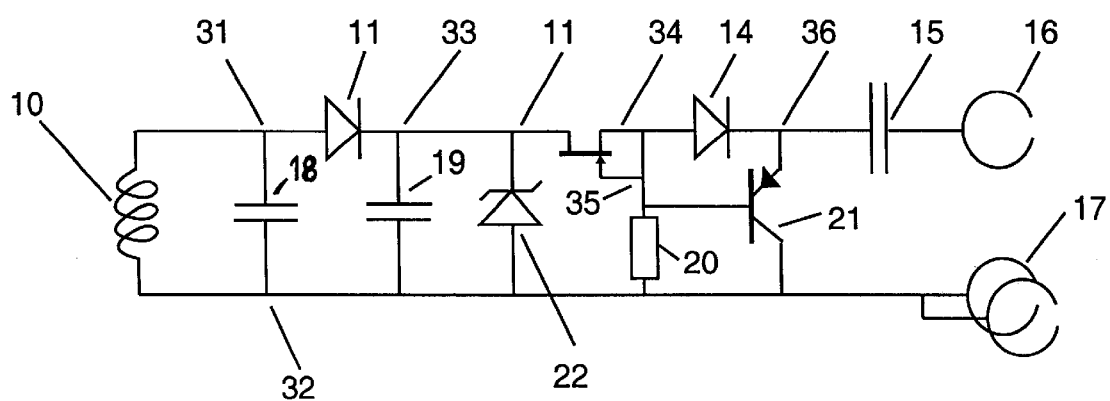
FIG. 2 illustrates, by means of an electrical schematic diagram, a preferred embodiment of the receiver portion of the stimulator.

Referring now to FIG. 2, there is shown a preferred embodiment of the receiver portion of the stimulator.

The receiver portion of this embodiment includes a receiver coil 10 in parallel with a capacitor 18 at junctions 32 and 31. The component values of the coil 10 and capacitor 18 are such that the circuit resonates at a selected receiver frequency.

A rectifier diode 11 is coupled to a filter capacitor 19 at a junction 33, which capacitor 19 is further connected to the common junction 32. The diode 11 rectifies an incoming signal and the filter capacitor 19 acts as a filter or bandpass filter for smoothing the signal and removing thigh frequency components of the rectified signal. Furthermore, a zener-diode 22 is coupled in parallel with the capacitor 19.

A JFET transistor 11 is coupled between the junction 33 and junctions 34, 35, the latter being connected to the gate of the JFET 11. The JFET transistor 11 limits the current to between 1 to 2 mA which is a sufficient stimulation current.

A resistor 20 is coupled between the junctions 35 and 32. A diode 14 is followed by a capacitor 15 connects an electrode 16 to the junction 35, and a transistor 21 is coupled to the junctions 35, 36 and 32.

The common junction 32 is furthermore coupled to two electrodes 17.

The circuit following the current limiting transistor 12 has the primary function of balancing the charge fed to the electrodes/put out on the electrodes, as the stimulation of a nerve bundle will have to be without any DC-components ensuring that the nerves are not damaged by the injected charge. The balancing circuit, thus secures that the charge lead into the stimulated nerve equals the charge taken out from the nerve.

The stimulation current is controlled by a current limiter consisting of the J-FET T2. As there is a great manufacturing spread in the drain current of these, the units which when measured are found to have a drain current between 1 and 2 mA are chosen. This circuit is principally sufficient when stimulating a nerve, however, since the nerve can be destroyed if only one polarity is stimulating the nerve, the pulses have to be charge balanced so that an equal amount of charge is drawn from the electrode as well as pumped into the electrode. This is ensured by the last part of the circuit. The transistor T1 is off as long as the transmitter is active. When the transmitter turns off, the voltage on C1 decreases which causes the base of T1 to be drawn low. While the pulse was sent, C3 was charged. This charge is now sent back through T1 which is on (D2 is blocking the other way) and backwards out through the electrode. As it is not possible to have a net DC current running through the capacitor (C3), a balanced stimulation is obtained ensuring that electro-chemical processes are not formed, which can destroy the tissue and the electrode. Zenerdiode Z1 is a protection against too high a voltage in the circuit, which might be caused by interfering magnetic fields in the relevant frequence area. When the voltage is limited, a powerful lasting external field will not be able to cause anything else but a single pulse on the electrode with a charge of Qmax=VZ×C3=9,1V×470 nF =4,3 $\mu$C which in extreme cases can give a single powerful stimulation pulse which, however, is not damaging to the nerve nor the electrodes. The level of activation of the nerve/muscle is modulated by varying the pulse duration. The width of the pulse is variable by means of external transmitters e.g. between 0–255 $\mu$s.

An external part of the stimulator, e.g. a corresponding telemetric transmitter (not shown), is constructed by means of known electrical elements.

In a preferred embodiment according to the invention, the transmitter generates an electromagnetic burst of sine-waves of approximately 5 MHz. The pulse is transmitted by two transmitting coils (shown in FIG. 4) each made of six windings of copper wire with a diameter of 0.375 mm, the coil diameter being approximately 90 mm. The coils can be positioned in such a way, that the implanted stimulator is located in the homogeneous field created between the two transmitting coils.

The coils can for example be located or incorporated in different kinds of clothing, such as stockings, trousers or the like.

It should be noted that the electrical components wholly or partly may be manufactures in an integrated circuit, such as ASIC-designs or the like.

Moreover, it should be noted that the electrical environment of the electrodes in many applications preferably may be digital, as a coded multichannel remote signal is free of crosstalk between the channels.

Figure 3:
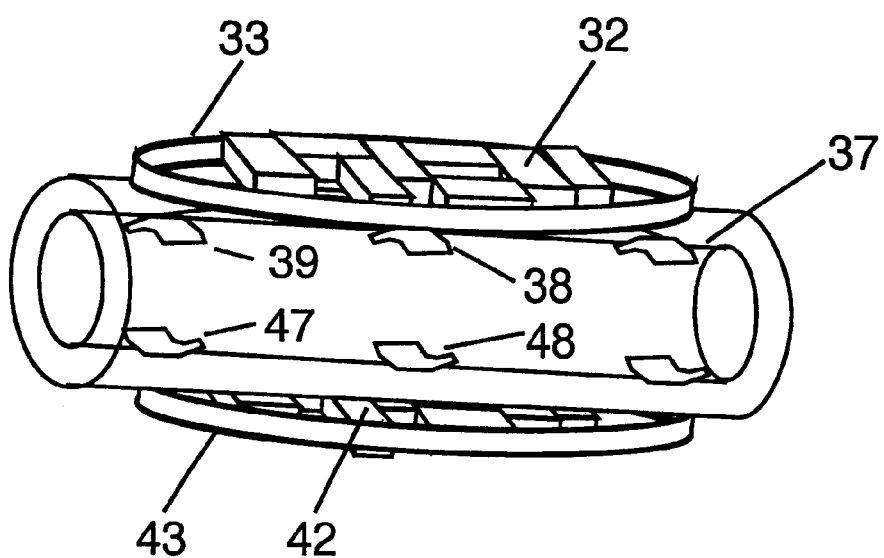
FIG. 3 illustrates a two channel stimulator according to the invention.

Referring now to FIG. 3, there is shown a stimulator according to the invention, said stimulator comprising a receiver coil 33, which is coupled to an electrical circuit 32. The electrical circuit 33 is furthermore connected to the dot electrodes 37, 38 and 39.

The stimulator further comprises a second receiver coil 43 which, in this embodiment, is coupled to a second electrical circuit 42. The second electrical circuit 43 is furthermore connected to the dot electrodes 47, 48 and 49.

The stimulator is thus a two channel stimulator with two separately operating receiving circuits, the circuits and the corresponding electrodes 31 and 41 being individually addressable. The electrodes are so-called dot-electrodes, which means that only a part of the ring-shaped electrode means is a electrode contact area in this embodiment. The stimulator is thus able to make a selective stimulation of the nerve and the associated muscles, when implanted around a nerve.

It is also possible within the scope of the invention to adapt the stimulator with several receiving channels. In one embodiment according to the invention the first receiving circuit is tuned to approximately 3.5 MHz and the second receiving circuit is tuned to approximately 4.7 MHz.

Figure 4:
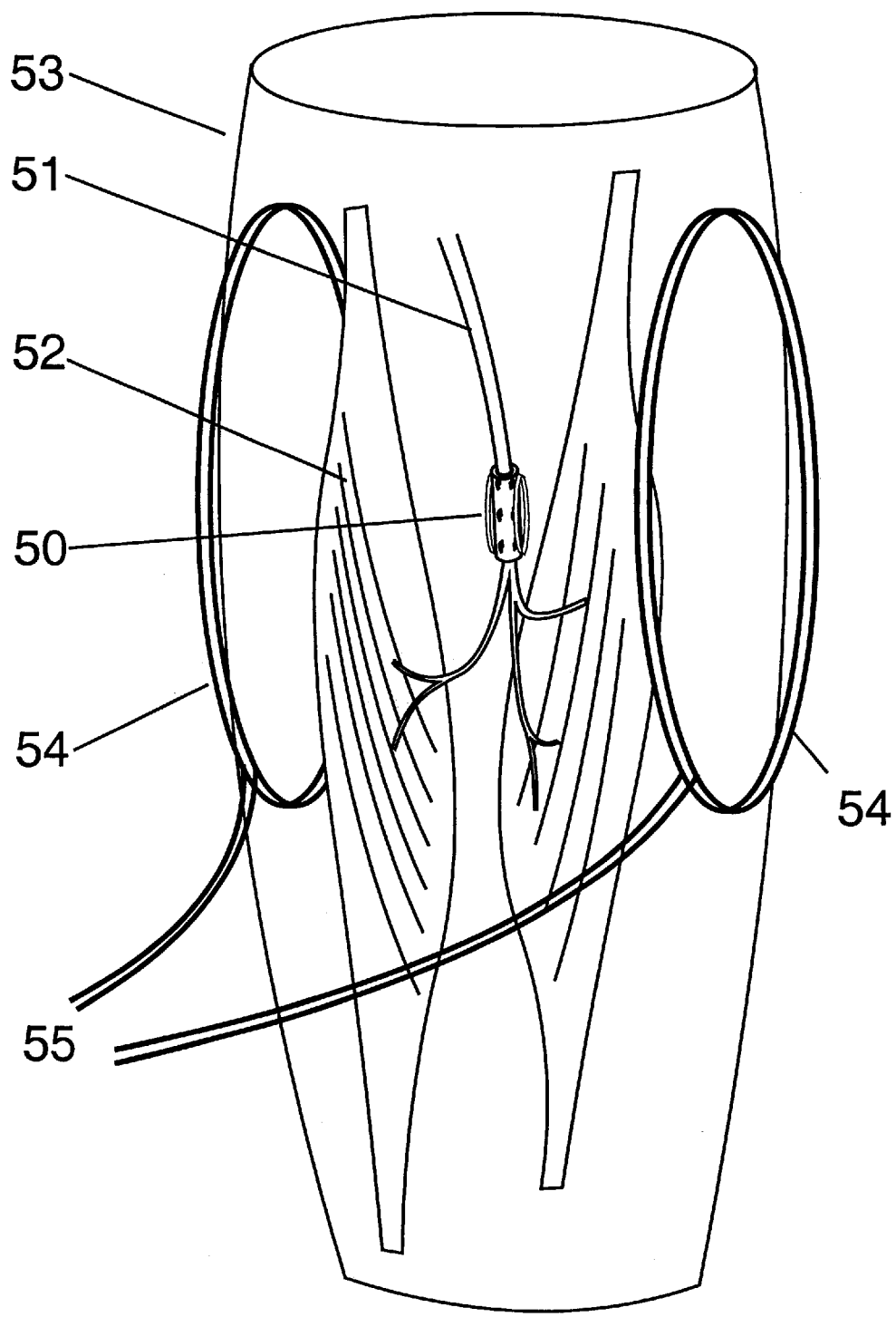
FIG. 4 shows a schematic drawing of a limb with stimulator and transmitter coils.

In FIG. 4 is shown how the stimulator 50 in FIG. 3 is mounted on the nerves 51 leading to the muscles 52 in a limb 53. As it is apparent from the drawing, two receiver coils 33 of the stimulator are placed parallel with the skin. The transmitter coils 54 are mounted in a bandage (not shown) placed around the limb. 55 designates the connection ends of the coils 54. The ends of the bandage are equipped with velcro-closing for fastening the bandage around the limb. The transmitter coils 54 are also lying flat on the skin and is considerably larger than the receiving coils on the stimulator. Due to the homogeneous electrical field and the size of same, the location of the transmitter coils on the limb is less significant.

The transmitter is operated by synchronous physiological signals e.g. suitably arranged switches or sensors. In case of a dropfoot patient by a heel switch or sensor.

According to the present invention the receiving coil and the stimulating circuitry can be embedded in the wall of a nerve cuff electrode. The transmitting coil consists preferably of two flat coils, which are placed externally on each side of the implanted stimulator. The device will work at shorter distances with only a single transmitter coil.

The simple electronic circuitry combined with the use of very small, but standard electronic components (surface mount components), makes it possible to sufficiently reduce the size of the circuit for it to be embedded in the wall of a nerve cuff. Further the simple electronic circuitry makes it possible to avoid the need for hermetic packaging, which is necessary if the circuit contains naked silicon chips.

Integration of the stimulator into a nerve cuff makes the necessary stimulation current very low. This means that the range of an external transmitter can easily be made large enough for the implant to be located deep within an extremity.

The receiving coils of the implanted stimulators lie parallel to the skin when implanted on a nerve, which makes it possible to use flat transmitting coils in the external transmitter. This is an advantage compared to other micro stimulators where the transmitting coil has to surround the implant. It means that the transmitting coil can easily be mounted on fabric and strapped onto/around the arm or leg with a velcro-closing or the like.

The use of two transmitting coils makes the range of the transmitter larger and the field more homogeneous, thus making the implanted stimulator less sensitive to movements with respect to the external transmitter. Accordingly, it is not significant that the transmitting coils are placed in the exact optimal position which can be difficult for the users who are typically disabled people who are paralysed in one side of their body The lack of lead wires makes the device less susceptible to damage, since malfunction of an implanted device is often caused by broken wires. Also the risk of damage to the nerve in the chronic implant is reduced, since nerve damage is often a result of the wires pulling on the electrode. Also the lack of wires renders the device more simple to install.

What is claimed is:

1. An implantable stimulator for stimulation of nerves and adapted to be surgically implanted around a nerve bundle, said stimulator comprising:

a housing in the form of a cuff, electrode means which, when implanted at least partially surrounds said nerve bundle, electronic circuit means having output terminals coupled to said electrode means, including input terminals for receiving an input signal, at least one receiving coil mounted on the housing, and wherein the input terminals are coupled to the at least one receiving coil.

2. An implantable stimulator according to claim 1, wherein the electrode means, when implanted around said nerve bundle, comprises at least one electrode at least partly surrounding the nerve bundle defining a contact area, each contact area being electrically coupled to the output terminals of the electronic circuit means.

3. An implantable stimulator according to claim 2 wherein the electrode means comprises three ring-shaped electrodes.

4. An implantable stimulator according to claim 1 wherein the electrode means, when implanted around said nerve bundle, comprises at least one ring-shaped electrode at least partly surrounding the nerve bundle, each ring-shaped electrode comprising at least two distinct electrode contact areas, each electrode area being electrically coupled to the output terminals of the electronic circuit means.

5. An implantable stimulator according to claim 1, wherein the electrode means comprises at least two electrode contact areas, the electronic circuit means comprises multi-channel pulse shaping electronics means, each input terminal being coupled to a separate receiving coil, each output terminal being coupled to a corresponding electrode contact area, said channels of said pulse shaping electronics means having a separate receiving frequency.

6. An implantable stimulator according to claim 1 wherein at least a portion of the stimulator is encapsulated within a biologically inert substance.

7. A transmitter/stimulator system comprising at least one transmitter and at least one implantable stimulator according to claim 1, each transmitter comprising a control circuit, said control circuit controlling and activating a transmitting stage, said transmitting stage converting electric signals to electromagnetic signals, wherein each transmitter comprises at least one transmitting coil adapted to be positioned in space relationship on each side of each of said at least one stimulator.

8. An implantable stimulator for stimulation of nerves and adapted to be surgically implanted around a nerve bundle, said stimulator comprising:

a housing, electrode means which, when implanted comprises at least one ring-shaped electrode at least partially surrounding said nerve bundle, electronic circuit means having output terminals coupled to said electrode means, including input terminals for receiving an input signal, at least one receiving coil mounted on the housing, and wherein the input terminals are coupled to the at least one receiving coil, said electrode further comprising at least two distinct electrode contact areas, each electrode area being electrically coupled to the output terminals of the electronic circuit means.

9. An implantable stimulator for stimulation of nerves and adapted to be surgically implanted around a nerve bundle, said stimulator comprising:

a housing, electrode means which, when implanted at least partially surrounds said nerve bundle, electronic circuit means having output terminals coupled to said electrode means, including input terminals for receiving an input signal, at least one receiving coil mounted on the housing, and wherein the input terminals are coupled to the at least one receiving coil, and wherein the electrode means further comprises at least two electrode contact areas, and the electronic circuit means further comprises multi-channel pulse shaping electronics means, each input terminal being coupled to a separate receiving coil, each output terminal being coupled to a corresponding electrode contact area, said channels of said pulse shaping electronics means having a separate receiving frequency.

* * * * *